United States Patent
Nanba et al.

(10) Patent No.: US 8,177,720 B2
(45) Date of Patent: May 15, 2012

(54) APPARATUS FOR DETECTING VITAL FUNCTIONS, CONTROL UNIT AND PULSE WAVE SENSOR

(75) Inventors: Shinji Nanba, Kariya (JP); Toshiaki Shiomi, Nagoya (JP)

(73) Assignees: DENSO CORPORATION, Kariya (JP); Toshiaki Shiomi, Nagoya (JP)

( * ) Notice: Subject to any disclaimer, the term of this patent is extended or adjusted under 35 U.S.C. 154(b) by 1342 days.

(21) Appl. No.: 11/802,607

(22) Filed: May 24, 2007

(65) Prior Publication Data

US 2007/0282227 A1 Dec. 6, 2007

(30) Foreign Application Priority Data

May 31, 2006 (JP) .................................. 2006-152354

(51) Int. Cl.
*A61B 5/02* (2006.01)
(52) U.S. Cl. ........................................ 600/483; 600/484
(58) Field of Classification Search .................. 600/483, 600/486, 500–504
See application file for complete search history.

(56) References Cited

U.S. PATENT DOCUMENTS

| | | | |
|---|---|---|---|
| 5,005,581 A | 4/1991 | Honeyager | |
| 5,704,367 A | 1/1998 | Ishikawa et al. | |
| 5,899,927 A | 5/1999 | Ecker et al. | |
| 6,083,157 A | 7/2000 | Noller | |
| 6,605,045 B2 | 8/2003 | Ohsaki et al. | |
| 6,669,632 B2 | 12/2003 | Nanba et al. | |
| 6,856,829 B2 | 2/2005 | Ohsaki et al. | |
| 2002/0183627 A1* | 12/2002 | Nishii et al. | 600/485 |
| 2004/0162499 A1 | 8/2004 | Nagai et al. | |
| 2006/0074334 A1 | 4/2006 | Coyle | |

FOREIGN PATENT DOCUMENTS

| | | |
|---|---|---|
| JP | A-7-000376 | 1/1995 |
| JP | A-8-173403 | 7/1996 |
| JP | A-9-098964 | 4/1997 |
| JP | A-2003-000552 | 1/2003 |
| JP | A-2003-038460 | 2/2003 |
| JP | A-2005-199078 | 7/2005 |

OTHER PUBLICATIONS

Office Action dated Aug. 15, 2008 from Chinese Patent Office in corresponding CN Patent Application No. 200710108768.0 (and English Translation).
Office Action mailed on Jul. 5, 2011 in the corresponding Japanese Patent application No. 2006-152354 (English translation enclosed).

* cited by examiner

*Primary Examiner* — Miranda Le
*Assistant Examiner* — Tho Tran
(74) *Attorney, Agent, or Firm* — Posz Law Group, PLC

(57) ABSTRACT

An apparatus for detecting vital functions has a pulse wave sensor attachable to a body and a control unit. The control unit checks if amplitude of pulse wave signals produced from the pulse wave sensor varies. The control unit further checks if a large change in the amplitude during a systolic phase of a pulse wave corresponding to the systolic phase of the heart. If a first large change in the amplitude during a diastolic phase of a pulse wave corresponding to the diastolic phase of the heart, it is highly probable that a motion artifact has occurred. Therefore, a motion artifact flag is set. Next, it is checked if the amplitude in the next diastole is changing by more than 30%. if it is presumed that the occurrence of cough is highly probable, a cough flag is set. if it is neither the motion artifact nor the cough, then a yawn flag is set.

26 Claims, 10 Drawing Sheets

MOTION ARTIFACT

APPARATUS FOR DETECTING VITAL FUNCTIONS, CONTROL UNIT AND PULSE WAVE SENSOR

CROSS REFERENCE TO RELATED APPLICATION

This application is based on and incorporates herein by reference Japanese Patent Application No. 2006-152354 filed on May 31, 2006.

FIELD OF THE INVENTION

This invention relates to a device for detecting vital functions, that is, biometric conditions, such as cough and yawn by using a pulse wave sensor that is easy to mount.

BACKGROUND OF THE INVENTION

A nasal thermistor, a nasal pressure sensor, a chest-band sensor and the like are respiratory system monitors for detecting breathing (respiration), cough and yawn.

As for measuring, for example, the cough, various devices using a spiro-breathing flow meter (patent document 1), signals of the thyroid (patent document 2) and vibration of a catheter (patent document 3). These measuring devices and measuring methods are so complicated that the cough and the like cannot be easily measured in private homes or vehicles.

As simpler technologies, it is proposed to use a pattern of voice signals detected by a microphone (patent document 4) or voice signals and a sound pressure level detected by a microphone (patent document 5). The accuracy of detection is low due to noise, and it is difficult to specify the source of sound when there is a plurality of persons.

It is also proposed to use a camera image of a nose (patent document 6) or variation in a bed load (patent document 7). In case of using the image, the image is taken at a particular position imposing limitation on the position for taking a measurement. Besides, a person puts his or her hand to a mouth when coughing. Therefore, the hand becomes a blind which lowers the accuracy of detection. In case of using the bed load, the motion artifact such as body motion cannot be separated from the cough.

As a method of detecting yawn, further, it is proposed to use a camera image or voice (patent document 8). This method requires a complicated measuring device. It is also proposed to detect respiration conditions by analyzing pulse waves (patent documents 9 to 11).

[Patent document 1] JP-A-8-173403
[Patent document 2] JP-A-9-98964
[Patent document 3] JP-T-11-506380 (U.S. Pat. No. 5,899,927)
[Patent document 4] JP-A-7-376
[Patent document 5] JP-A-2003-38460
[Patent document 6] JP-A-8-257015 (U.S. Pat. No. 5,704,367)
[Patent document 7] JP-A-2003-552
[Patent document 8] JP-A-2005-199078
[Patent document 9] JP-A-2002-355227 (U.S. Pat. No. 6,669,632)
[Patent document 10] JP-A-2002-78690 (U.S. Pat. No. 6,856,829)
[Patent document 11] JP-A-2002-153432 (U.S. Pat. No. 6,856,829)

SUMMARY OF THE INVENTION

The present invention has an object of providing an apparatus for detecting vital functions such as cough and yawn based on a simple method, a control unit therefor and a device for mounting a pulse wave sensor unit.

(1) According to a first aspect of the invention, it is determined that a motion artifact has occurred when the amplitude—during a diastolic phase of a pulse wave ("on p-diastole side" for short)—corresponding to the diastolic phase of the heart has exceeded a predetermined lower-limit level that corresponds to the lowest blood pressure.

Through experiments, it was confirmed that the motion artifact has occurred if the amplitude on p-diastole side falls below the lower-limit level as shown in FIG. 3A.

Namely, the minimum blood pressure (the diastolic blood pressure) is maintained by the elasticity of blood vessels, and it does not happen that the amplitude on p-diastole side suddenly becomes lower than the lower-limit level as observed based upon the pulse wave signals. If a signal of a pulse wave lower than the diastolic blood pressure appears, therefore, it is regarded that the motion artifact has occurred. In the diagram illustrating the pulse waves, the upper side is expressed to be the side of systole and the lower side is expressed to be the side of diastole for easy comprehension relative to the blood pressure (diagram which is usually called inverted pulse waves).

As the lower-limit level for determining the intensity on p-diastole side, for example, an approximated line can be employed that is found from a plurality of peaks on p-diastole side representing the diastolic blood pressure. However, values that are increased or decreased by a predetermined percentage may be selected as the lower-limit level.

(2) According to a second aspect of the invention, a respiration waveform (respiration curve) that represents the respiration condition is found from the pulse waves. It is determined that a cough has occurred when a double triangular wave of an acute angle is detected, in which two peaks of the respiration waveforms are consecutively exceeding a predetermined level.

If a cough occurs, a double triangular wave of an acute angle lower than a predetermined level (since the thoracic pressure has a negative sign, the respiration waveforms in the graph are expressed protruding downward) is observed within a short period of time (e.g., within 1 to 2 seconds) as shown in FIG. 5B due to the motion of muscles specific to coughing. Therefore, the above conditions are used for determining the coughing. Here, the double triangular wave of an acute angle has acute angles that are formed by the lines on the outer sides of the right and left peaks.

In case the amplitude of the respiration waveform has increased by more than, for example, 30% beyond the normal amplitude, it is probable that a coughing has occurred. Therefore, there may be added another determining condition, i.e., if the amplitude is greater than a predetermined level. Further, the predetermined level (or the predetermined period) used for the determination can be set by finding an optimum value through experiment (the same holds hereinafter).

(3) According to a third aspect of the invention, it is determined that a cough has occurred when the amplitude—during a systolic phase of a pulse wave ("on p-systole side" for short)—corresponding to the systolic phase of the heart has exceeded a predetermined level (predetermined level on p-systole side) and when the amplitude on p-diastole side corresponding to the succeeding diastolic phase of the heart has exceeded a predetermined level (predetermined level on p-diastole side).

If a cough has occurred, a peak of the pulse wave signal on p-systole side once greatly rises as shown in FIG. 5A and, immediately thereafter, the peak on p-diastole side greatly falls. Therefore, this condition is employed as a condition for determining the coughing.

(4) According to a fourth aspect of the invention, it is determined that a cough has occurred when the amplitude on p-systole side corresponding to the systolic phase of the heart has increased by more than a predetermined level (beyond, for example, the normal amplitude on p-systole side) without causing the waveform of the pulse waves to be varied (distorted or broken in shape) from the waveform of ordinary pulse waves.

If the couth has occurred as shown in FIG. 5A, the amplitude on p-systole side rises without causing the pulse waves to vary. Therefore, this condition is employed as a condition for determining the coughing.

As a method of determining a case where the waveform of the pulse wave varies from the ordinary waveform, there can be employed, for example, a method of obtaining a correlation between the waveforms of pulse waves. For example, waveforms of several pulse waves in an ordinary state free of motion artifact or coughing are averaged to obtain a representative waveform of pulse waves, which is, then, recorded, while a correlation of a waveform of a wavelength or of a plurality of wavelengths is obtained relative to the pulse wave that is to be compared. If the correlation is, for example, not larger than 0.7, it can be so determined that the waveform of the pulse wave has varied. In addition to the correlation, there can be employed the analysis of peak-to-peak pitch variation of the pulse waves or the analysis of chaos.

(5) According to a fifth aspect of the invention, it is determined that a cough has occurred when a change in the ratio (AW2/BW2) of the amplitude (AW2) of the base level of a pulse wave/amplitude (BW2) of a pulse wave is within a predetermined level (e.g., a change is within 30% of when there is no motion artifact) and when the time of change is within a predetermined period (e.g., 1 to 2 seconds corresponding to the coughing).

The probability of coughing is high if the above condition is satisfied. Therefore, this condition is employed here as a condition for determining the coughing.

(6) According to a sixth aspect of the invention, it is more reliably determined that a coughing has occurred when a motion artifact is not detected than when the motion artifact is detected while determining the occurrence of coughing based on at least one cough determining method among the above cough determining methods.

The occurrence of coughing and the intensity of coughing can be determined more accurately when a plurality of cough determining methods are used in combination than when the cough determining method of any one of the above aspects is used.

(7) According to a seventh aspect of the invention, it is determined that a yawn has occurred when the base level of a pulse wave is lowered over a predetermined period corresponding to the yawning.

If a yawing has occurred, the base level of pulse waves is mildly lowered as shown in FIG. 7A due to the motion of muscles specific to the yawning. Therefore, the base level of pulse waves remains lowered for a predetermined period (e.g., 4 to 12 seconds). Therefore, this condition is employed as a condition for determining the yawning.

As a case where the base level is lowered for a predetermined period, there can be employed a period in which the base level is in a lowered state or a period in which the base level is in a state lower than a certain determining value (period of the sum of being lowered and elevated).

(8) According to an eighth aspect of the invention, it is determined that a yawn has occurred when the amplitude of pulse waves has become smaller than a predetermined level (predetermined level for determining the amplitude of pulse waves) within a period in which the base level of pulse waves is lower than a predetermined level (predetermined level for determining the base level).

When the base level of pulse waves has increased from the lowered state as shown in FIG. 7A, the amplitude of pulse waves (whole amplitude in the up-and-down direction) decreases due to the motion of muscles specific to the yawning. Therefore, this condition is employed as a condition for determination to further improve the accuracy of determination.

(9) According to a ninth aspect of the invention, it is determined that a yawn has occurred when the amplitude on p-systole side corresponding to the systolic phase of the heart exceeds a predetermined level (predetermined level on p-systole side) but the amplitude on p-diastole side corresponding to the diastolic phase of the heart does not become smaller than a predetermined level (predetermined level on p-diastole side).

If a yawn has occurred, a peak on p-systole side slightly increases as shown in FIG. 7A due to the motion of muscles specific to the yawning. However, a peak of the pulse wave on the side of the expansion period immediately thereafter does not become lower than the normal value (the peak, usually, increases slightly). Therefore, this condition is employed as a condition for determining the yawning.

(10) According to a tenth aspect of the invention, it is determined that a yawn has occurred when the whole amplitude of pulse waves becomes smaller than a predetermined level (predetermined level for determining the whole amplitude) after the amplitude on p-systole side corresponding to the systolic phase of the heart has exceeded a predetermined level (predetermined level for determining the amplitude on p-systole side) without causing the waveform of pulse waves detected by a pulse wave sensor to be varied from the waveform of ordinary pulse waves.

When a yawn occurs as shown in FIG. 7A, a peak on p-systole side slightly increases and, thereafter, the amplitude of pulse waves decreases without causing the pulse waves to be varied. Therefore, this condition is employed as a condition for determining the yawning.

(11) According to an eleventh aspect of the invention, a respiration waveform representing the respiration state is found from the pulse waves. It is determined that a yawn has occurred when the amplitude of the respiration waveform is not smaller than a predetermined level (predetermined angle for determining the amplitude) and when a double triangular wave of an obtuse angle is detected in which two peaks of the respiration waveform are consecutively exceeding a predetermined level (predetermined level for determining the peak).

If a yawn has occurred as shown in, for example, FIGS. 8A to 8C, a double triangular wave of an obtuse angle (of larger than a predetermined amplitude) occurs, in many cases, on the respiration waveform. Therefore, this condition is employed here as a condition for determining the yawning.

Here, the double triangular wave of an obtuse angle stands for a double triangular wave in which the angle formed by lines on the outer sides of the right and left peaks is an obtuse angle.

(12) According to a twelfth aspect of the invention, it is determined that a cough has occurred when a change in the ratio (AW2/BW2) of the amplitude (AW2) of the base level of a pulse wave/amplitude (BW2) of a pulse wave is not smaller than a predetermined level and when the time of change is within a predetermined period corresponding to the yawning.

As shown in FIG. 7, it was clarified that the probability of yawning is high when the change of the ratio (AW2/BW2) is not smaller than a predetermined level and when the time of change is within a predetermined period (e.g., 4 to 12 seconds) corresponding to the yawning. Therefore, this condition is employed here as a condition for determining the yawning.

(13) According to a thirteenth aspect of the invention, it is more reliably determined that a yawn has occurred when a motion artifact is not detected than when the motion artifact is detected while determining the occurrence of the yawn based on at least one yawn determining method among the above yawn determining methods.

The occurrence of yawning and the intensity of yawning can be more accurately determined when a plurality of yawn determining methods are used in combination than when the yawn determining methods of any one of the above aspects is used.

(14) A fourteenth aspect of the invention exemplifies preferred methods for determining the motion artifact.

Described below is another example of methods for determining the motion artifact.

It can be determined that the motion artifact has occurred in case the waveform of the pulse waves has varied from the waveform of the ordinary pulse waves.

That is, in case the motion artifact has occurred, vary of the pulse waves is observed as shown in FIG. 3A. If such a change is detected, therefore, it can be so determined that the motion artifact has occurred. The ordinary pulse waves are pulse waves in a calm state where there is no such changes as motion artifact, cough or yawn.

A respiration waveform (respiration curve) that represents the respiration state is found from the pulse waves. It is so determined that the motion artifact has occurred if the amplitude of the respiration waveform has changed by more than a predetermined level and if the waveform of a pulse wave has varied from the waveform of the ordinary pulse waves.

That is, in case the motion artifact has occurred, a change in the amplitude of the respiration waveform is observed as shown in FIG. 3B in addition to the vary of the waveforms. In case such a change is detected, it may be so determined that the motion artifact has occurred.

Here, as described in the above patent document 9, a first variation signal representing a varying state from the pulse wave is found, a second variation signal representing a varying state of the first variation signal is found, and the respiration waveform (respiration curve) is found based on a difference between the first variation signal and the second variation signal.

As the first variation signal as shown in FIG. 2, there can be employed a first envelope that connects the peaks of waveforms of signals of pulse waves or a first amplitude ratio line that connects the points dividing the amplitudes of waveforms of signals of pulse waves by a predetermined ratio. As the second variation signal, further, there can be employed a second envelope that connects the peaks of waveforms of the first variation signals or a second amplitude ratio line that connects the points dividing the amplitudes of waveforms of the first variation signals by a predetermined ratio.

It can be determined that a motion artifact has occurred when a ratio (AW2/BW2) of the amplitude (AW2) of the base level of a pulse wave/amplitude (BW2) of a pulse wave has changed by more than a predetermined level, the change being of a nature of a single-shot and when the time of change is outside a predetermined period (shorter than, for example, 4 seconds or longer than, for example 12 seconds) that corresponds to the yawning.

Namely, as will be described later, when the ratio (AW2/BW2) of the amplitude (AW2) of the base level of a pulse wave/amplitude (BW2) of a pulse wave has changed by more than a predetermined level, it is probable that a yawning is occurring. However, when the change is of a nature of a single-shot and the period of change is different from the period of the case of yawning, it was clarified through experiments that the probability of motion artifact is high.

Whether the change is of a nature of a single-shot can be determined based on if the change has occurred only once within a preset period (e.g., 20 seconds).

Referring to FIG. 7A, further, the amplitude (AW2) of the base level of the pulse waves stands for a width of deviation from the center of the base level while the amplitude (BW2) of the pulse waves represents the whole width in the up-and-down direction of the pulse waves. As the amplitude of the base level of the pulse waves, however, there can be employed the hole amplitude in the up-and-down direction of the base level.

When it is determined by a plurality of motion artifact-determining method that a motion artifact has occurred, it can be more reliably determined that the motion artifact has occurred than when it is not.

That is, the accuracy of determination can be more improved when a plurality of motion artifact determinations are combined together than when each of the above motion artifact determinations is used.

As described above in detail, the apparatus for detecting the conditions of a body of the second to fourteenth aspects detects the cough or yawn by utilizing signals obtained through a pulse wave sensor, i.e., easily detects the cough or yawn (or deep respiration) in private homes or vehicle compartments based on a method simpler than the conventional methods.

In the above aspects, the pulse waves can be measured from an arm or a finger in addition to the face by using the pulse wave sensor offering a distinguished effect of cleanly taking a monitoring at a portion kept away from the cough, spit or phlegm that could become a cause of infectious disease to the respiratory systems.

On account of each time of cough or yawn can be detected, it is allowed to find the number of coughs and yawns (to render a quantitative evaluation). Based on the number theory, therefore, it is also allowed to diagnose the degree of symptom such diseases as chronic bronchitis or whooping cough, or to detect the sign of sleepiness.

(15) According to a fifteenth aspect of the invention, when the occurrence of cough or yawn is determined by the above various methods for determining the cough or yawn (inclusive of definite cough determining method definite yawn determining method), various actuators are controlled such as adjusting the temperature and blow rate of an air conditioner, offering a guide by the navigation system or varying the state of the seat and the seat belt based upon the results of determination, for example, upon the symptoms so as to relax the coughing or to promote the recovery from the sleepiness.

That is, an alarm is produced as required, or the environment is controlled being linked to the air conditioner. Further, the disease is determined based on the determined results of coughing and yawning. If it is a cold, the temperature and humidity are suitably set. If it is an allergic rhinitis, the air in the compartment may be replaced with the fresh external air or an auxiliary filter may be operated. Further, the data of the determined results may be stored to be used for controlling the health and for the diagnosis by a doctor.

(16) In a sixteenth aspect of the invention, further, if a pulse wave sensor is of an optical type, a buffer member is arranged between the pulse wave sensor and the skin so that the optical device of the skin side does not come in contact with the skin or pushes the skin with a pressure which is not larger than a predetermined level.

This restricts the pulse wave sensor from pushing the skin with an excess of pressure, and the blood circulation is not restricted. Therefore, the measurement can be taken accurately.

(17) According to a seventeenth aspect of the invention, a sponge having a rugged pattern on the skin side may be used as the preferred buffer member.

(18) In an eighteenth aspect of the invention, if the pulse wave sensor is of the optical type, an elastic member may be arranged on the pulse wave sensor on the side opposite to the skin for mounting the pulse wave sensor on the surface of the body, so that the optical device pushes the skin with a pressure which is not larger than a predetermined level.

This prevents the pulse wave sensor from pushing the skin with an excess of pressure. Therefore, an excess of load is not given to the skin, the waveforms of pulses are not distorted, and the pulse waves can be accurately measured.

(19) A nineteenth aspect of the invention uses a band (for example, a rubber material or an expansible bandage) as a preferred elastic member for fixing the pulse wave sensor to the body.

(20) A twentieth aspect of the invention uses a member (for example, a spring or the like) as a preferred elastic member for fixing the pulse wave sensor to the body.

BRIEF DESCRIPTION OF THE DRAWINGS

The above and other objects, features and advantages of the present invention will become more apparent from the following detailed description made with reference to the accompanying drawings. In the drawings.

DESCRIPTION OF THE PREFERRED EMBODIMENTS

Figure 1A:
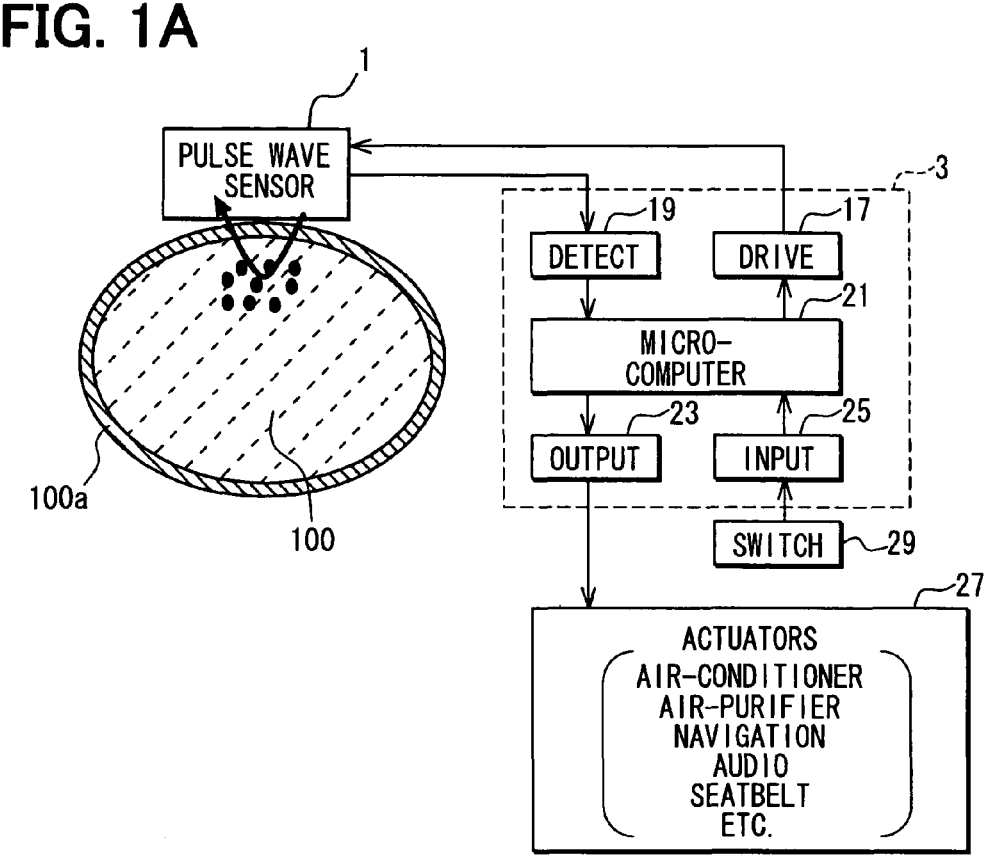
FIG. 1A is a schematic diagram illustrating an apparatus for detecting the conditions of a body and a mounting device therefor according to an embodiment.
Figure 1B:
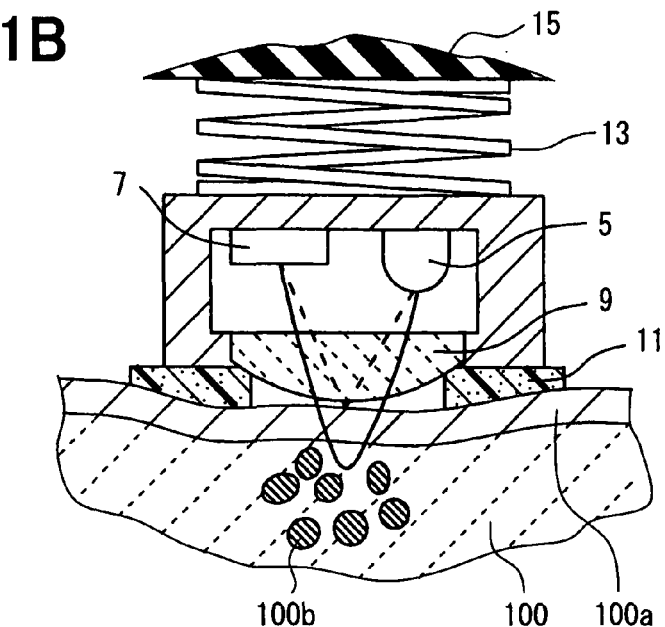
FIG. 1B is an enlarged schematic view illustrating a pulse wave sensor used in the embodiment.

First, a biometric detection apparatus for detecting conditions of a body is described with reference to one embodiment shown in FIGS. 1A and 1B. The apparatus detects vital functions such as cough or yawn by using a pulse wave sensor 1. This sensor 1 is attached to a portion of a human body 100 such as a finger, a palm or a wrist, where motion is small. The apparatus further uses a control unit 3, which drives the pulse wave sensor 1 and processes the outputs from the pulse wave sensor 1.

Here, the pulse wave sensor 1 is an optical sensor of the reflection type (opto-capacitive pulse wave sensor) comprising a light-emitting element (e.g., light-emitting diode: green LED) 5, a light-receiving element (e.g., photodiode: PD) 7, and a transparent lens 9 which permits light to pass through and also efficiently receives light.

The pulse wave sensor 1 has a ring-like buffer member (e.g., a sponge having a rugged end) 11 that serves as a spacer surrounding the lens 9 on the skin side so that the lens 9 will not be pushed onto the skin 100a with an excess of pressure, and a spring 13 on the rear end side of the pulse wave sensor 1. This makes it possible to set the pressure for pushing the lens 9 onto the skin 100a to be not larger than 10 gw/cm$^2$. The pulse wave sensor 1 is fixed to the wrist or the like by using a band 15. Therefore, the spring 13 is arranged between the band 15 and the pulse wave sensor 1.

When the pulse wave sensor 1 is to be used, a driving electric power is supplied from a drive unit 17 in the control unit 3 and light is projected to the human body from the light-emitting element 5. Part of the light hits capillary vessels (capillary arteries) in the human body, is absorbed mostly by hemoglobin in the blood flowing through the capillary vessels, while rest of the light scatters repetitively and partly falls on the light-receiving element 7. Due to the pulsation of blood at this moment, the amount of hemoglobin in the capillary vessels vary periodically like a wave and, therefore, the light absorbed by the hemoglobin varies like a wave, too.

As a result, the amount of light absorbed by the capillary vessels varies and, accordingly, the amount of light received or detected by the light-receiving element 7 varies. A change in the amount of the received light is output as pulse wave data (sensor output which is a voltage signal representing the pulse wave) to the control unit 3.

The control unit 3 includes the drive unit 17, a detector unit 19 that receives a sensor output, a microcomputer 21 which produces a control signal to the drive unit 17 and to an output unit 23 and receives signals from the detector unit 19 and from an input unit 25 to execute various processing, the output unit 23 that sends control signals to various actuators 27, and the input unit 25 that receives a signal from a manual switch 29.

The microcomputer 21 is an electronic circuit including known CPU, ROM, RAM and the like, and incorporates a program for detecting the coughing and yawning by processing pulse wave signals applied from the pulse wave sensor 1.

The pulse wave sensor 1 may be attached to any part of the body but is desirably attached to an arm, hand, finger, forehead or foot that is less affected by the motion artifact.

Next, the principle for detecting the coughing and yawning will be described with reference to FIGS. 2A to 8F. In these figures, the abscissa represents the passage of time and the ordinate represents the magnitude (intensity or variation) of the signals.

Figure 2A:
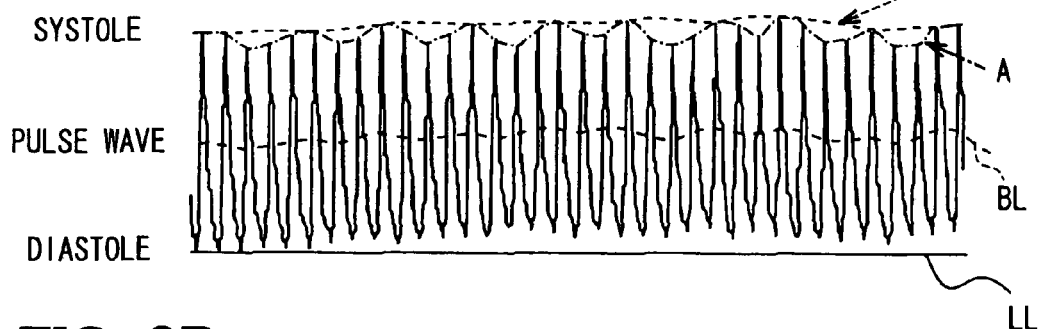
FIG. 2A is a graph illustrating a waveform of pulse waves.

Referring first to FIG. 2A, the pulse wave sensor 1 produces pulse wave signals having peaks corresponding to the systolic phase and to the diastolic phase of the heart. Specifically, varying peaks appear in the upper side in the figure during the systolic phase of the heart, and varying peaks appear in the lower side in the figure during the diastolic phase of the heart.

During the ordinary calm state, i.e., when there is no motion artifact, cough or yawn, and there is only a very mild variation of a large period due to the motion of the blood vessels, variation of the blood pressure in the blood vessels is slow. As a result, the peaks of signals on p-diastole side do not become lower than a predetermined low-limit level LL (line corresponding to the lowest blood pressure).

As a method of setting the lower-limit level LL, there can be exemplified an approximated line found, for example, from a plurality of peaks on p-diastole side representing the lowest blood pressure.

Figure 2B:
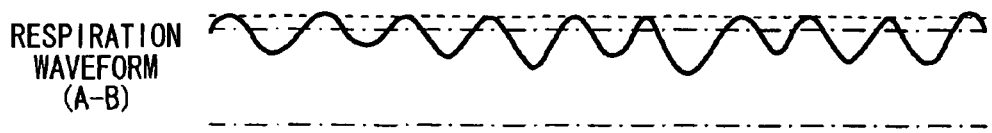
FIG. 2B is a graph illustrating a respiration waveform.

A line connecting the centers of the upper and lower peaks of pulse wave signals is called the base level BL (index related to an average blood pressure). Further, a line connecting the peaks of signals on p-systole is called a pulse wave envelope (first envelope) A, and a line connecting the peaks of the first envelope is called a double envelope (second envelope) B. Referring to FIG. 2B, a waveform found by subtracting the second envelope B from the first envelope A is called a respiration waveform (respiration curve). The respiration waveform is a signal corresponding to the intra-thoracic pressure.

The principle of the processing of the embodiment conducted by using the above signals is described next.

(1) Method of Detecting Motion Artifact

Figure 3A:
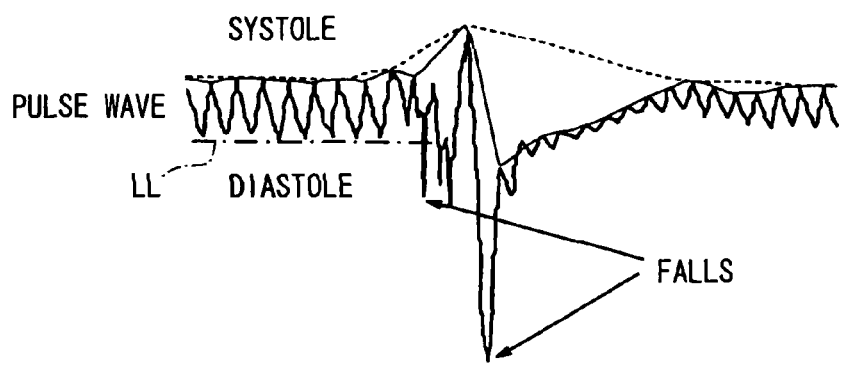
FIG. 3A is a graph illustrating a waveform of pulse waves of when there is a motion artifact.
Figure 3B:
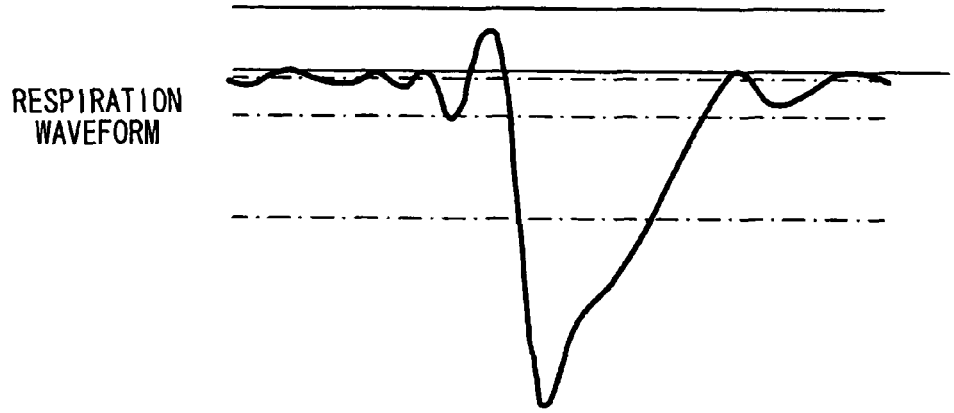
FIG. 3B is a graph illustrating a respiration waveform of when there is a motion artifact.

Referring to FIG. 3A, when a motion artifact has occurred, the pulse wave on p-diastole side, first, so varies as to becomes lower than (fall below) the lower-limit level LL from the ordinary (calm) pulse waves, i.e., from the state of the regular sinusoidal pulse wave signals. The frequency of pulse wave signals of this period becomes smaller than the frequency of the ordinary pulse wave signals (of when there is no motion artifact) (e.g., state of high-frequency noise) and the waveforms, in many cases, greatly vary from the sinusoidal waves.

If the signal on p-diastole side exceeds the lower-limit level LL, therefore, it can be so determined that the motion artifact has occurred. Here, if the waveform varies or the frequency of pulse wave signals becomes small, it is highly probable that the motion artifact has occurred.

Figure 4A:
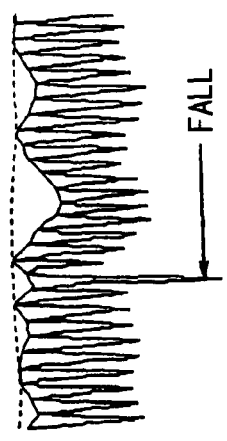
FIG. 4A is a graph illustrating a waveform of pulse waves of when there is a strong motion artifact.
Figure 4B:
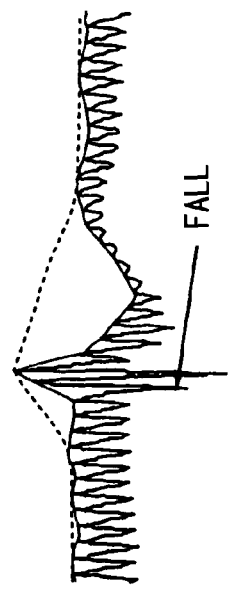
FIG. 4B is a graph illustrating a respiration waveform of when there is a strong motion artifact.
Figure 4C:
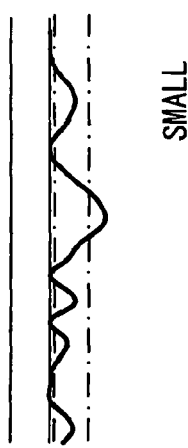
FIG. 4C is a graph illustrating a waveform of pulse waves of when there is a motion artifact of an intermediate degree.
Figure 4D:
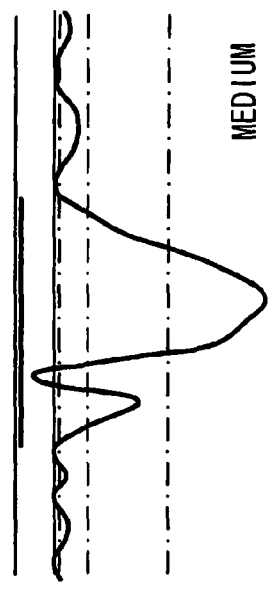
FIG. 4D is a graph illustrating a respiration waveform of when there is a motion artifact of an intermediate degree.
Figure 4E:
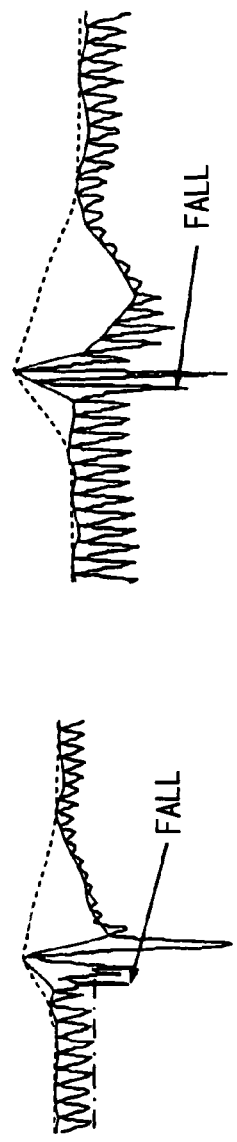
FIG. 4E is a graph illustrating a waveform of pulse waves of when there is a weak motion artifact.
Figure 4F:
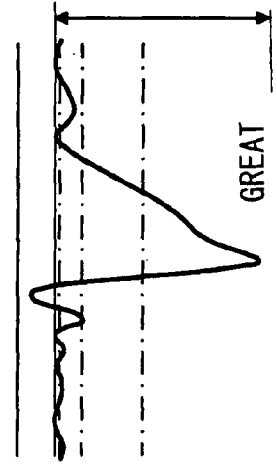
FIG. 4F is a graph illustrating a respiration waveform of when there is a weak motion artifact.

Referring to FIGS. 4B, 4D and 4F, further, the respiration waveform found from the peaks on p-systole differs depending upon the intensity (strength) of the motion artifact. Therefore, the intensity of motion artifact can be determined from the state of the respiration waveform. If the motion artifact is great, for example, the respiration waveform falls greatly and a curve thereof becomes sharp as shown in FIG. 4B. If the motion artifact is medium, the respiration waveform falls greatly but a curve thereof becomes loose. If the motion artifact is small, the respiration waveform falls little.

Accordingly, the motion artifact can be accurately detected by each of the following determining methods (algorithms) or by a combination of the determining methods. The following determining methods have all been confirmed through the practically conducted experiments (the same also holds for the coughing and yawning).

In case the amplitude on p-diastole side has increased (i.e., in case the peaks of amplitude on p-diastole side have exceeded a predetermined level or have become smaller than the lower-limit level LL, it is determined that the motion artifact has occurred (motion artifact flag T1 is set as described later).

In case the waveform of pulse waves has varied from the sinusoidal wave, it is determined that the motion artifact has occurred. Whether the waveform has varied from the sinusoidal waves can be determined based on a correlation to the waveform of the ordinary (e.g., preceding) pulse wave. For example, it can be regarded that the waveform has varied if a coefficient of the correlation is not larger than 0.7.

In case the amplitude of the respiration waveform has varied and the waveform of pulse waves has varied from the sinusoidal waves, it can be determined that the motion artifact has occurred. Here, if the waveform has varied from the sinusoidal waves can be determined based on a correlation to the waveform of the ordinary pulse waves (for example, it can be regarded that the waveform has varied if a coefficient of the correlation is not larger than 0.6).

In case there is a change in the amplitude AW2 of the base level BL divided by the amplitude BW2 of pulse waves (FIG. 7), the change is a nature of a single-shot and the time of change is as short as 0 to 4 seconds or as long as 12 seconds or more, it is determined that the motion artifact has occurred (motion artifact flag T3 is set as described later).

A change from the sinusoidal waves or a change in the amplitude can be determined from the analysis of variation in the peak-to-peak pitch or from the analysis of chaos in addition to utilizing the correlation (the same holds hereinafter).

(2) Method of Detecting Cough

Figure 5A:
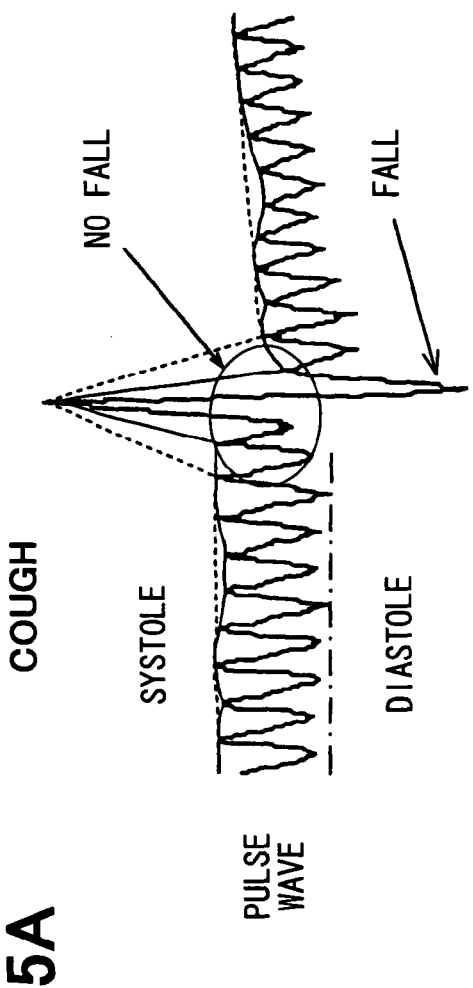
FIG. 5A is a graph illustrating a waveform of pulse waves of when a cough has occurred.

Referring to FIG. 5A, if the cough has occurred, the amount of terminal blood temporarily increases due to instantaneous contraction of muscles accompanying the coughing. The pulse wave on p-systole side, first, increases greatly from the state of ordinary pulse wave signals.

The coronary veins are compressed by the abdominal muscles that have tensed due to coughing, the blood returning to the heart instantaneously decreases. The heart blows out the blood in decreased amounts. Accordingly, the pulse wave on p-systole side immediately after the rise falls greatly in excess of the lower-limit level. The time of coughing is so short that there is no change in the amplitude of the pulse wave signals, and the base level readily restores. In the case of the coughing, usually, no change is seen in the frequency and there is almost no change in the shape of the sinusoidal waves, either.

Figure 5B:
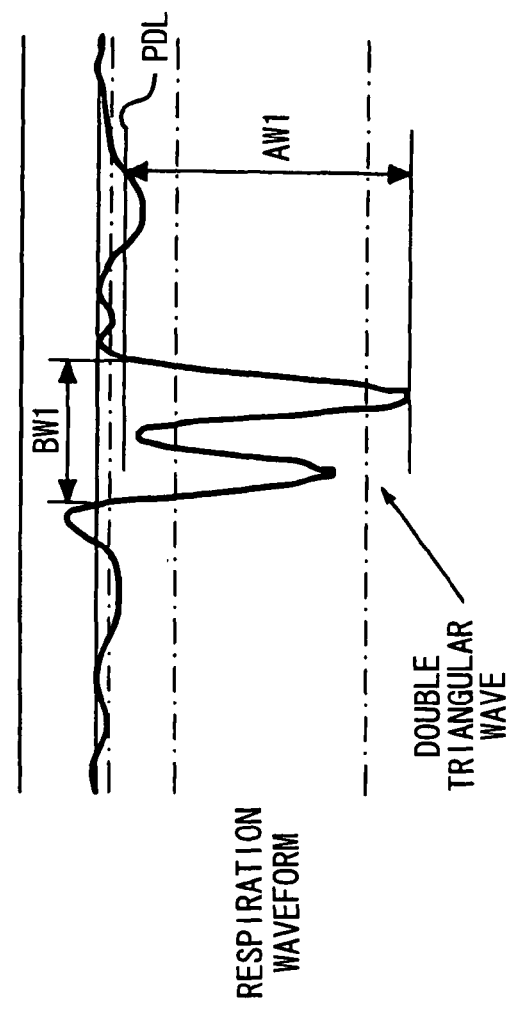
FIG. 5B is a graph illustrating a respiration waveform of when a cough has occurred.

In case the cough occurs, further, a double waveform (double triangular wave) of a characteristic acute angle appears on the respiration waveform obtained from the pulse waves as shown in FIG. 5B. A large ratio (AW1/BW1) of the longitudinal width (amplitude) AW1 and the transverse width (period) BW1 of the double triangular wave represents an intense coughing in which the intrathoracic pressure sharply changes within a short period of time.

What makes the double triangular wave may be determined relying, for example, upon "if the determining line is exceeded that is separated away from the ordinary line of the respiration waveform by more than a predetermined percentage".

Therefore, if the pulse wave on p-systole side, first, greatly increases (in excess of the predetermined upper-limit level) and, immediately thereafter, the pulse wave on p-diastole side exceeds the lower-limit level, it can be determined that the cough has occurred. Further, if the double triangular wave appears on the respiration waveform, it can be determined that the cough has occurred.

Figure 6A:
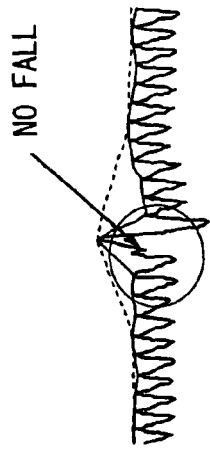
FIG. 6A is a graph illustrating a waveform of pulse waves of when a strong cough has occurred.
Figure 6C:
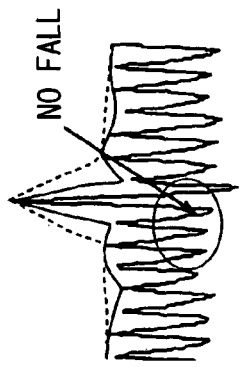
FIG. 6C is a graph illustrating a waveform of pulse waves of when a cough of an intermediate degree has occurred.
Figure 6E:
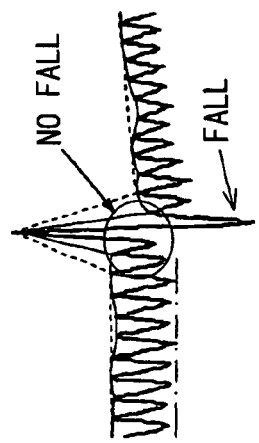
FIG. 6E is a graph illustrating a waveform of pulse waves of when a weak cough has occurred.
Figure 6B:
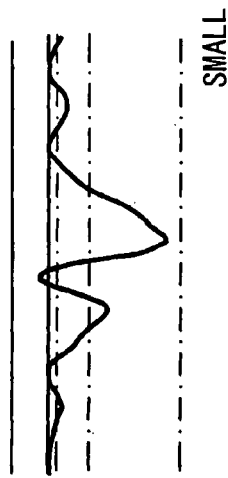
FIG. 6B is a graph illustrating a respiration waveform of when a strong cough has occurred.
Figure 6D:
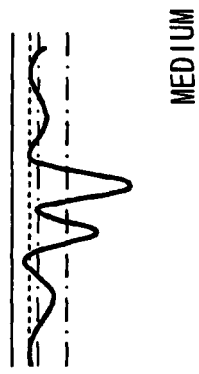
FIG. 6D is a graph illustrating a respiration waveform of when a cough of an intermediate degree has occurred.
Figure 6F:
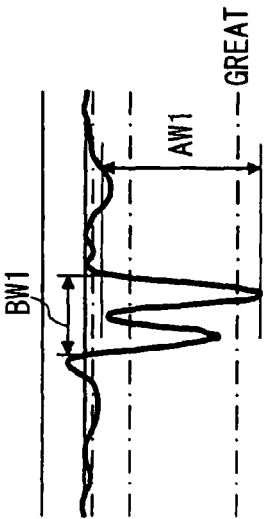
FIG. 6F is a graph illustrating a respiration waveform of when a weak cough has occurred.

Referring to FIGS. 6A to 6F, further, the pulse wave signal and the respiration waveform differ depending upon the intensity of coughing. From the states thereof, therefore, the intensity of coughing can be checked if the coughing is intense, for example, the pulse wave signals vary greatly in the up-and-down direction as shown in FIG. 6A, the respiration waveform falls greatly as shown in FIG. 6B, and the ratio AW1/BW1 becomes large. If the coughing is of the medium degree, further, the pulse wave signals vary up and down to a slightly large extent as shown in FIG. 6C, the respiration waveform falls to a medium degree as shown in FIG. 6D, and the ratio AW1/BW1 is of a medium degree. Further, if the coughing is weak, the pulse wave signals vary up and down to a small degree, and the respiration waveform falls mildly.

Thus, the coughing can be accurately detected by the combination of one or two or more kinds of the following determining methods.

If the amplitude on p-systole side increases (i.e., if the peak of amplitude increases on p-systole side) and the amplitude on p-diastole side increases (i.e., if the peak of amplitude is lowered on p-diastole side), it is determined that the coughing has occurred (cough flag S1 is set as described later).

If the amplitude on p-systole side increases (i.e., if the peaks increase on p-systole side only) without causing the waveform of pulse waves to be varied from the sinusoidal waves, it can be regarded that the cough has occurred.

If the amplitude of the respiration waveform varies (increases by 30% above the normal value) and a double waveform of an acute angle appears on the respiration waveform, it is determined that the coughing has occurred (cough flag S2 is set as described later).

If (amplitude AW2 of the base level/amplitude BW2 of the pulse waves) of pulse waves varies little (decreased by 30% below the normal) and the time of change is shorter than a predetermined level (e.g., shorter than 4 seconds), it is determined that the cough has occurred.

Here, it is important that in detecting the coughing, the motion artifact is determined, too. Even in case it is determined that the cough has occurred by the above determining method, it is determined that the cough has occurred only when it is so determined that there is no motion artifact. This is to isolate the motion artifact from the cough to render an accurate determination.

(3) Method of Detecting Yawn (Deep Respiration)

Figure 7A:
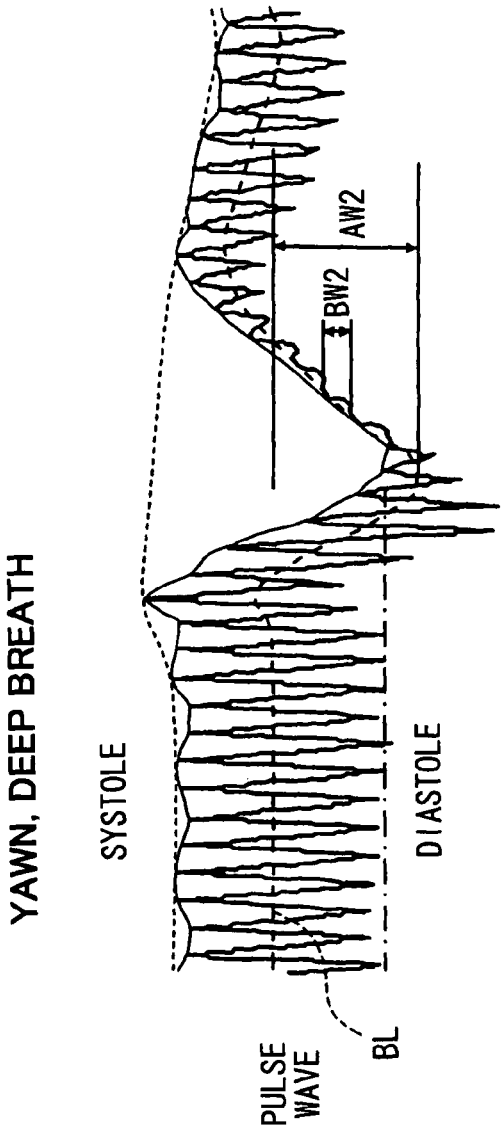
FIG. 7A is a graph illustrating a waveform of pulse waves of when a yawn has occurred.

Referring to FIG. 7A, if the yawn (or deep respiration) has occurred, the amount of terminal blood temporarily increases to some extent due to mild contraction of muscles accompanying the yawn. Therefore, the systolic pulse wave, first, increases to some extent from the ordinary state of pulse wave signals.

Thereafter, the coronary veins are compressed by the abdominal muscles that have tensed due to coughing, the blood returning to the heart gradually decreases. Therefore, the heart blows out the blood in decreased amounts for several seconds. Accordingly, the base level of the pulse wave signals gradually decreases. At this moment, the base level gradually decreases as designated at AW2 in proportion to the intensity of yawning, and the amplitude BW2 of the pulse waves decreases.

The reflux of blood to the heart is squeezed for several seconds due to the yawning, and about 10 seconds are needed before the pulse wave is recovered. In the case of the yawning, the sinusoidal waves of pulse wave signals do not change much, and a double triangle of an obtuse angle having a wide bottom side is seen on the respiration waveform.

It can be determined that the yawn has occurred based on a decrease in the base level of pulse wave signals, on a decrease in the respiration waveform (e.g., based on a decreased state lasting for 4 to 12 seconds) or on a decrease in the amplitude of pulse waves.

Figure 8E:
FIG. 8E is a graph illustrating a waveform of pulse waves of when a weak yawn has occurred.
Figure 8C:
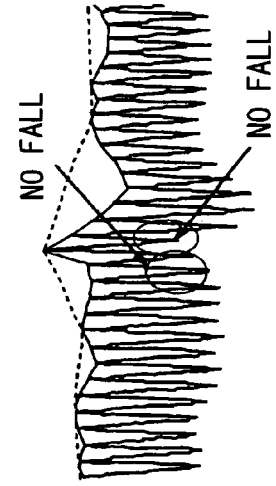
FIG. 8C is a graph illustrating a waveform of pulse waves of when a yawn of an intermediate degree has occurred.
Figure 8A:
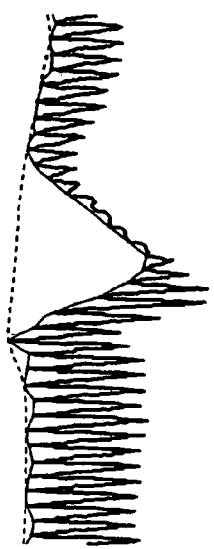
FIG. 8A is a graph illustrating a waveform of pulse waves of when a strong yawn has occurred.
Figure 8F:
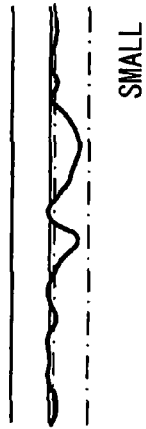
FIG. 8F is a graph illustrating a respiration waveform of when a weak yawn has occurred.
Figure 8D:
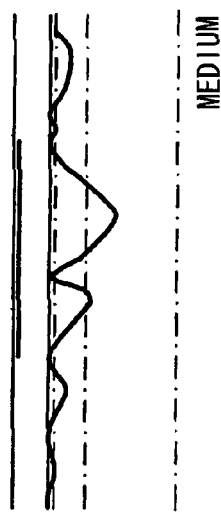
FIG. 8D is a graph illustrating a respiration waveform of when a yawn of an intermediate degree has occurred.
Figure 8B:
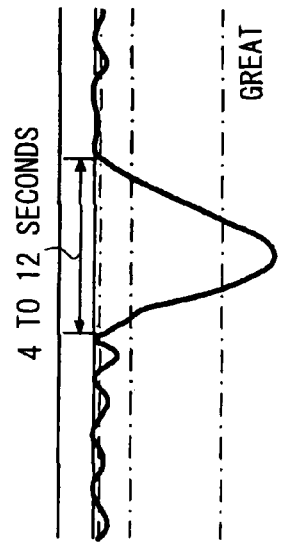
FIG. 8B is a graph illustrating a respiration waveform of when a strong yawn has occurred.

Referring to FIGS. 8A to 8F, further, the pulse wave signal and the respiration waveform differ depending upon the intensity of yawning. From the states thereof, therefore, the intensity of yawning can be checked if the yawning is intense, for example, the pulse wave signals and the respiration waveform fall greatly as shown in FIGS. 8A and 8B. Besides, the width of fall is great (4 to 12 seconds) and the amplitude of pulse wave signals becomes considerably small after the fall as shown in FIG. 8A. If the yawning is of the intermediate degree, further, the pulse wave signals and the respiration signals fall to a medium degree as shown in FIGS. 8C and 8D. Besides, the width of fall is of a medium degree and the amplitude of the pulse wave signals does not change much as shown in FIG. 8C. Further, if the yawning is weak, the pulse wave signals and respiration signals fall little or the width of fall is small as shown in FIGS. 8E and 8F, and the amplitude of the pulse wave signals does not change much as shown in FIG. 8E.

Therefore, the yawning can be accurately detected by the combination of one or two or more kinds of the determining methods.

If the waveform on p-systole increases (i.e., if the peak of pulse waves during systole increases) but the peak of pulse waves on the side of the next diastole does not become smaller than that of the ordinary case, it is determined that the yawn has occurred (yawn flag A1 is set as described later).

If the amplitude on p-systole side increases and, thereafter, if the whole amplitude BW2 of pulse waves decreases without causing the waveform of pulse waves to vary from the sinusoidal waves, it is determined that the yarn has occurred.

If the amplitude of the respiration waveform varies and a double curve of an obtuse angle appears on the respiration waveform, it is determined that the yawn has occurred (yawn flag A2 is set as described later).

If the ratio AW2/BW2 (amplitude AW2 of the base level divided by amplitude BW2 of the pulse waves) of pulse waves varies greatly (larger by 30% or more above the normal) and the time of change is longer than a predetermined value (e.g., longer than 8 seconds), it is determined that the yawn has occurred.

It is important that in detecting the yawn, the motion artifact is determined, too. Even in case it is determined that the yawn has occurred by the above determining method, it is determined that the yawn has occurred only when it is so determined that there is no motion artifact. This is to separate the motion artifact from the yawning to render an accurate determination.

Next, processing executed by the control unit 3 based on the above principles will be described with reference to flowcharts of FIGS. 9 to 12.

These processing employs some of the above determining methods to finally determine the occurrence of the motion artifact, coughing and yawning.

Figure 9:
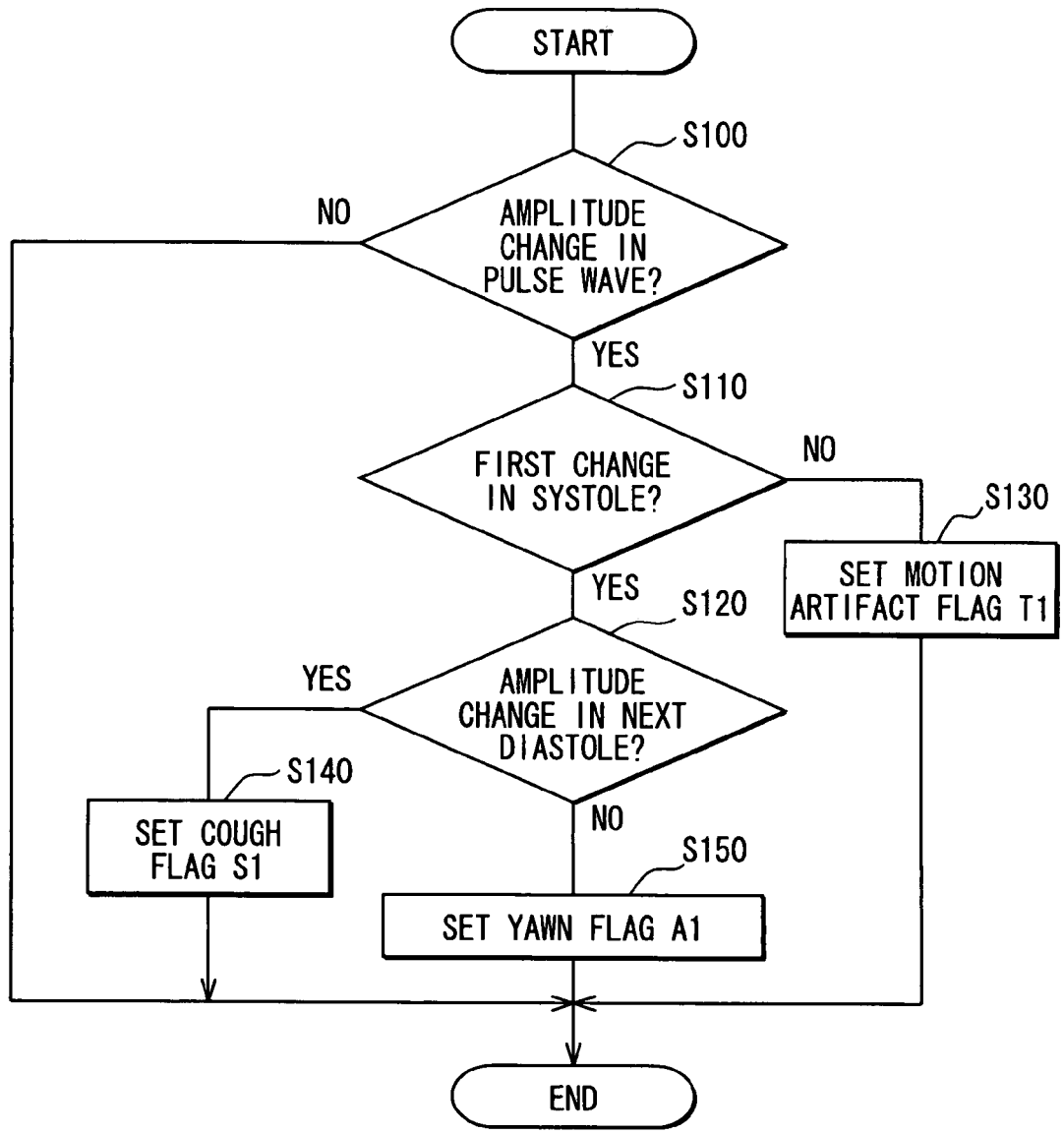
FIG. 9 is a flowchart illustrating processing for setting flags T1, S1 and A1.

(I) Referring to FIG. 9, it is checked at step (S) 100 if there is a change in the amplitude of pulse wave signals produced by the pulse wave sensor 1. Specifically, it is checked if the amplitude of pulse wave signals is varying up and down by not less than 30% beyond the up-and-down amplitude of the ordinary pulse wave signals, or if the amplitude on p-systole side (or the amplitude on p-diastole side) is varying by not less than 30% beyond the amplitude of the ordinary pulse wave signals on p-systole side (or beyond the amplitude on p-diastole side). If the determination is affirmative, the routine proceeds to step 110. If the determination is negative, the processing once ends.

That is, if the amplitude exceeds by more than 30% beyond the amplitude of the ordinary pulse wave signals, it can be presumed that motion artifact, coughing, yawning or the like, which is different from the ordinary calm state, has occurred.

At step 110, it is checked if a large change in the amplitude detected at step 100 is on p-systole side. If the determination is affirmative, the routine proceeds to step 120, if the determination is negative, the routine proceeds to step 130.

When a first large change in the amplitude (peak protruding downward) is on p-diastole side, it is highly probable that the motion artifact has occurred as shown in FIG. 3A. Therefore, at step 130, a motion artifact flag T1 is set to represent the above fact, and the processing once ends.

If the first large change in the amplitude is on p-systole side, the probability of motion artifact is low. It is, therefore, probable that the cough or the yawn has occurred. It is checked at step 120 if the amplitude in the next diastole is varying by more than 30%. If the determination is affirmative, the routine proceeds to step 140. If the determination is negative, the routine proceeds to step 150.

If the amplitude in the next diastole is varying by more than 30%, as shown in FIG. 5A, it can be presumed that the cough has occurred highly probably. That is, the pulse wave signals are, first, greatly varying on p-systole side and, immediately thereafter, are greatly varying on p-diastole side. Thus, it is presumed that the probability of cough is high. A cough flag S1 is set at step 140 to represent the above fact, and the processing once ends.

If neither the motion artifact nor the cough is occurring, based on the elimination method, it is presumed that the above variation in the pulse wave signals at step 100 above is caused by the yawning. Therefore, a yawn flag A1 is set at step 150 to represent the above fact, and the processing once ends.

If there is a large change in the pulse wave signals, the flag of any one of the motion artifact, coughing or yawning can be set based on the state where the pulse wave signals are varying.

Figure 10:
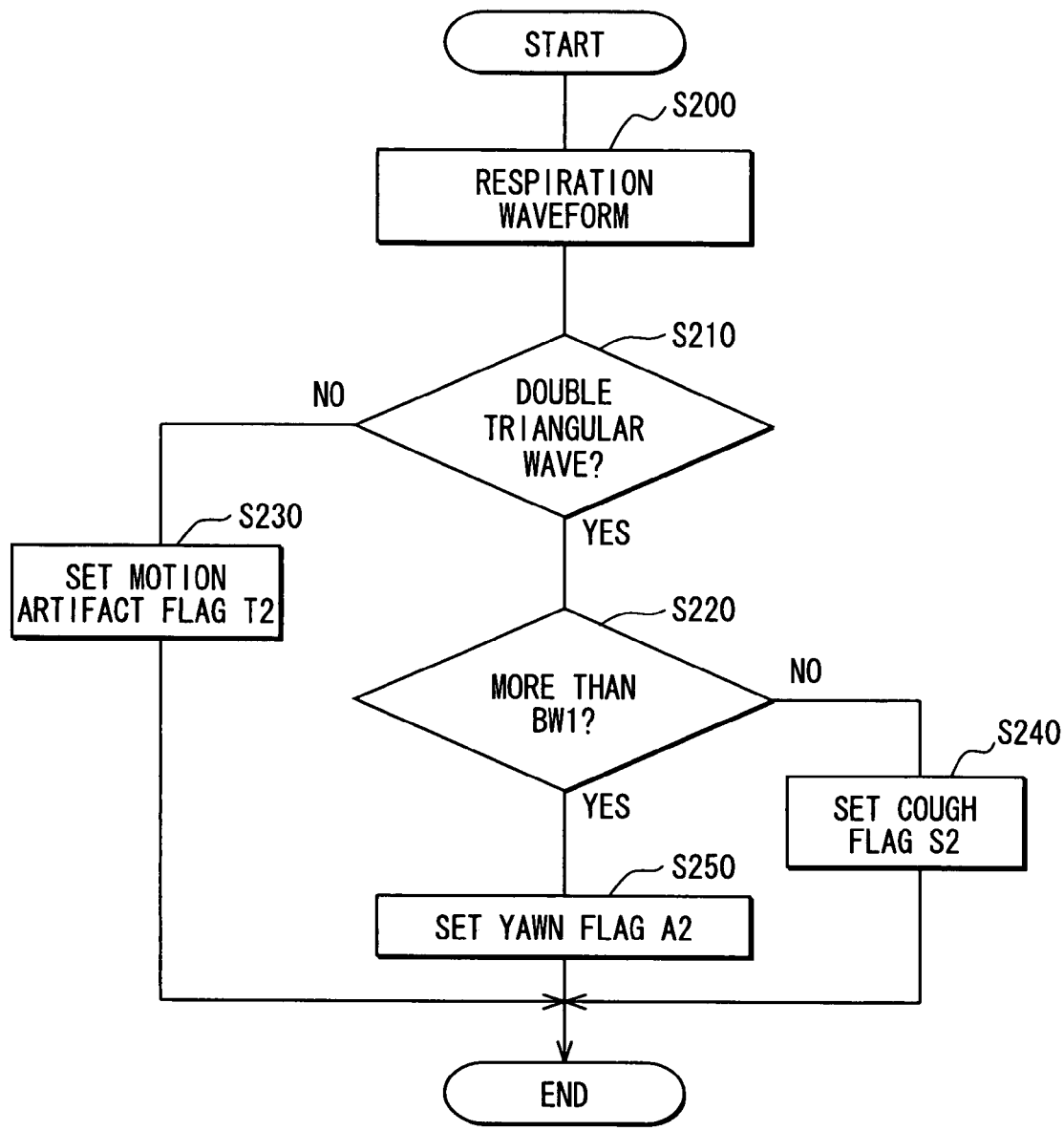
FIG. 10 is a flowchart illustrating processing for setting flags T2, S2 and A2.

(II) Referring to a flowchart of FIG. 10, a respiration waveform (respiration curve) is generated or formed at step 200 based on the pulse wave signals produced from the pulse wave sensor 1.

At subsequent step 210, it is checked if there is a double triangular wave on the respiration curve. Specifically, it is checked if there is a W-shaped waveform (waveform having a protrusion on the upper side) under the predetermined determining level of the respiration curve as shown in FIG. 5B. If the determination is affirmative, the routine proceeds to step 220. If the determination is negative, the routine proceeds to step 230.

If there is no double triangular wave, it is presumed that there is the motion artifact and the motion artifact flag T2 is set at step 230 to once end the processing.

At step 220, it is checked if the double triangular wave is a double triangular wave of an obtuse angle of more than a predetermined time width BW1 (e.g., 4 seconds at the predetermined determining level PDL). Namely, it is checked here if the double triangular wave has an obtuse angle by checking the predetermined width BW1. If the determination is affirmative, the routine proceeds to step 250. If the determination is negative, the routine proceeds to step 240.

Here, the addition of a condition "a change in the amplitude of the pulse wave curve is greater than the normal value by more than 30%" further improves the accuracy of determination.

If the double triangular wave has an acute angle as shown in FIG. 5B, it is highly probable that the cough has occurred. Therefore, a cough flag S2 is set at step 240 to represent the above fact, and the processing once ends.

If the double triangular wave is not of an acute angle, it is highly probable that the yawn has occurred instead of the cough (without motion artifact). Therefore, a yawn flag A2 is set at step 250 to represent the above fact, and the processing once ends.

If there is a large change in the respiration curve, a flag of any one of the motion artifact, coughing or yawning is set based on the state of change in the respiration curve.

Figure 11:
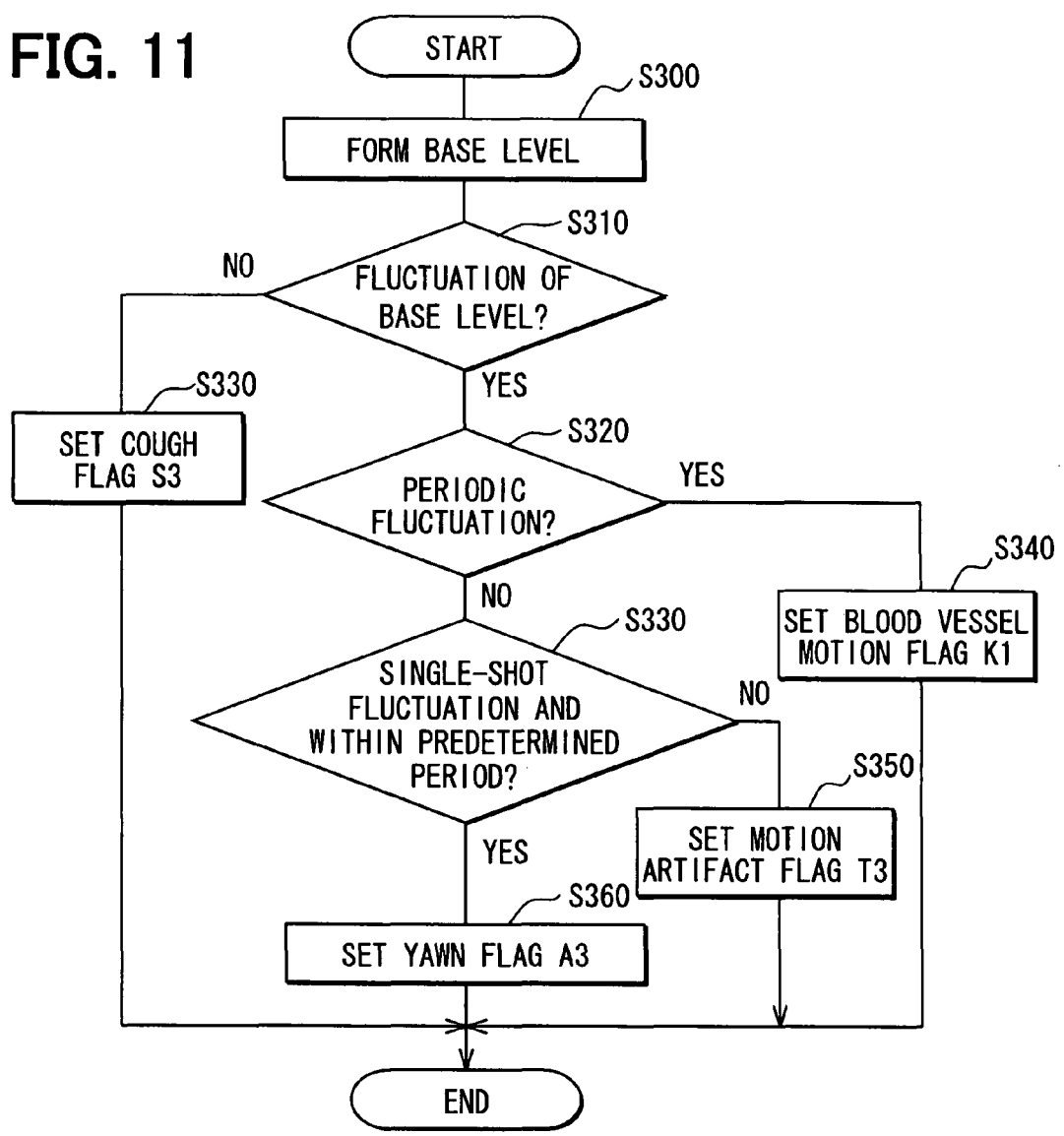
FIG. 11 is a flowchart illustrating processing for setting flags T3, S3 and A3.

(III) Referring to a flowchart of FIG. 11, a base level (line) BL is formed based on the pulse wave signals produced from the pulse wave sensor 1.

At subsequent step 310, it is checked if the base level of the pulse waves is fluctuating. Specifically, as shown in FIG. 7A, it is checked if ration AW2/BW2 (amplitude AW2 of the base level (herein, amplitude from an average value of the base level in normal operation) divided by amplitude BW2 of each pulse wave signal) is greater than a predetermined determining value (e.g., if the change is greater than the normal value by more than 30%). If the determination is affirmative, the routine proceeds to step 320. If the determination is negative, the routine proceeds to step 330.

If there is no fluctuation in the base level BL, a cough flag S3 is set at step 330 presuming that the cough has occurred, and the processing once ends.

It is checked at step 320 if the base level is fluctuating periodically (at a period of, for example, 6 to 15 seconds). If the determination is affirmative, the routine proceeds to step 340. If the determination is negative, the routine proceeds to step 330.

If the period of fluctuation of the base level is long, it is so determined that the fluctuation is arising from the motion of blood vessels. A blood vessel motion flag K1 is set at step 340 to represent the above fact, and the processing once ends.

At step 330 it is checked if the fluctuation of the base level is of a nature of a single-shot and is within a predetermined period (e.g., 4 to 12 seconds). If the determination is affirmative, the routine proceeds to step 360. If the determination is negative, the routine proceeds to step 350.

Figure 7B:
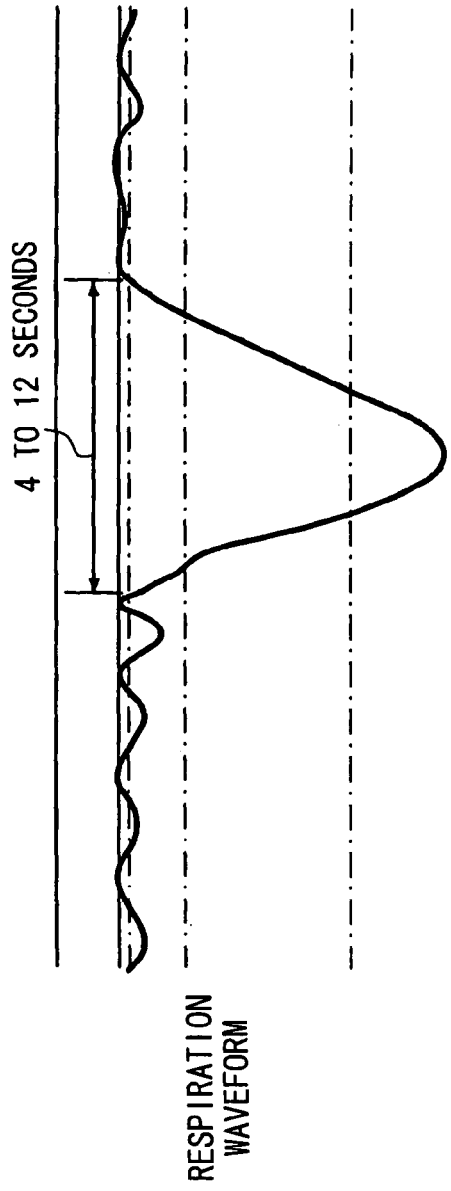
FIG. 7B is a graph illustrating a respiration waveform of when a yawn has occurred.

If the fluctuation of the base level is of the nature of a single-shot and is within the predetermined period (e.g., 4 to 12 seconds) as shown in FIG. 7B, it can be presumed that the yawn has occurred. Therefore, a yawn flag A3 is set at step 360, and the processing once ends.

If the fluctuation is not a single-shot or more than the predetermined period, a motion artifact flag T3 is set at step 350 presuming that the motion artifact may have occurred, and the processing once ends.

The fluctuation of the base level is thus analyzed, and the flag of any one of the motion artifact, coughing or yawning is set.

Figure 12:
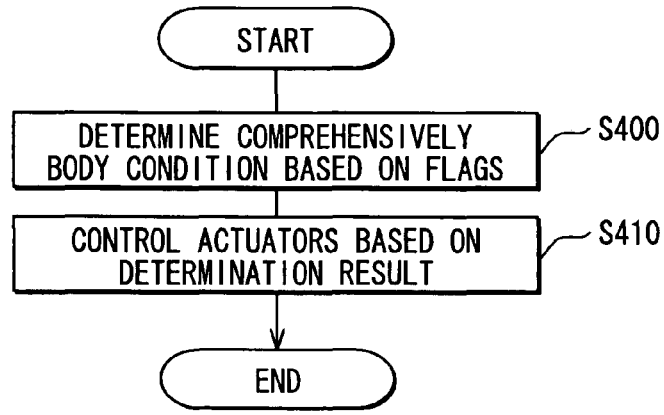
FIG. 12 is a flowchart illustrating control processing based on a comprehensive determination of the motion artifact, coughing and yawning.

(IV) Referring to a flowchart of FIG. 12, vital function, such as respiration and pulsation is comprehensively determined based on the flags.

For example, when three kinds of motion artifact flags T1 to T3 are set, it can be reliably determined that the motion artifact has occurred. Further, when one or two flags are set among the three kinds of motion artifact flags T1 to T3, it may be so determined that the motion artifact has occurred. The reliability of motion artifact increases with an increase in the kinds of the flags that are set. Among the three kinds of motion artifact flags T1 to T3, there is a flag which highly represents the motion artifact (e.g., motion artifact flag T1). If this flag is set, it may be so determined that the motion artifact has occurred. Alternatively, a large threshold value may be set to the counter for the motion artifact flag that represents a high probability. The motion artifact may be determined based on a total value of the motion artifact flags counted by the counter.

What is described above holds even for the three kinds of cough flags S1 to S3 and yarn flags A1 to A3. If the cough flag S1 is set, it is most probable that the cough has occurred. If the yawn flag A3 is set, it is most probable that the yawn has occurred.

Even if it is determined that the cough or the yawn has occurred based on the cough flags S1 to S3 or the yawn flags A1 to A3, it may be often determined that the motion artifact has occurred based on the motion artifact flags T1 to T3. In such a case, it is not determined that the cough or the yawn has occurred but, instead, it is determined that the motion artifact has occurred, reducing erroneous determination.

At next step 410, actuators are controlled, such as the air conditioner, navigation system, seats, seatbelts, etc. based on the above determined results, and the processing once ends.

The following processing can be employed for controlling the actuator.

For example, disorders of respiration such as asthma and emphysema of the lungs, disorders of inspiration such as rhinitis and nasal congestion, and cold can be presumed from the frequency and intensity of coughing, number of beats, number of breaths, a curve of respiration and fluctuation in the respiration (respiration signals). The air conditioner, air cleaner, navigation system, audio equipment, seats and seat belts are adjusted depending upon the symptoms that are presumed.

Specifically, the following control operations may be executed, for example.

If the cough is detected while an alarm of ear pollen has been issued, the conditioned air in the compartment is switched to the air-recirculation mode (internal circulation mode), and an auxiliary filter such as an air-purifier is operated. If the coughing occurs more frequently than usual, it is so presumed that the person is having a slight cold, the compartment temperature and the humidity are set to be slightly higher. Further, if the yawn is frequently detected, information is produced from the navigation system to stimulate the driver's brain to prevent him from becoming sleepy. If the yawn still occurs too frequently, the tension of the seat belt is varied to stimulate the body to keep the person awake.

In addition to the above results of presumption, other pulse wave data (pulse waveform, fluctuation in the pulse wave amplitude, pulse rate, variation in the interval between pulses, etc.) may be added or any other body data signals (blood pressure, electrocardiograph, electromyograph, camera image) may be added to presume the condition of the body at that moment to correct the control of air-conditioner, air-purifier, navigation system, audio equipment, seats and seatbelts.

The present invention is not limited to the above embodiments only but can be put into practice in a variety of other ways.

What is claimed is:

1. An apparatus for detecting vital functions, comprising:
    sensing means adapted for attachment to a body and produces pulse wave signals corresponding to pulse waves of the body; and
    respiration waveform calculation means for finding a respiration waveform that represents a respiration condition from the pulse waves detected by the sensing means; and
    cough determining means which determines an occurrence of a cough when formation of a double triangular wave is detected, the double triangular wave having an acute angle in which two peaks of the respiration waveform consecutively exceed a predetermined level.

2. An apparatus for detecting vital functions according to claim 1, further comprising:
    motion artifact determining means which determines an occurrence of a motion artifact based on the pulse waves detected by the sensing means, wherein
    the cough determining means determines the occurrence of the cough when the motion artifact determining means additionally determine no occurrence of the motion artifact.

3. The apparatus according to claim 1, wherein the sensing means includes:
    an optical device for projecting light onto a skin of the body to measure the pulse waves of the body; and
    a buffer member arranged between the optical device and the skin so that the optical device of the skin side does not come in contact with the skin or pushes the skin with a pressure which is less than a predetermined level.

4. An apparatus for detecting vital functions, comprising:
    sensing means adapted for attachment to a body and produces pulse wave signals corresponding to pulse waves of the body; and
    cough determining means which determines an occurrence of a cough when an amplitude of the pulse waves on a p-systole side corresponding to a systolic phase of a heart of the body has exceeded a predetermined level and when the amplitude of the pulse wave signals on a p-diastole side corresponding to a succeeding diastolic phase of the heart of the body has exceeded a predetermined level.

5. The apparatus according to claim 4, wherein the sensing means includes:
    an optical device for projecting light onto a skin of the body to measure the pulse waves of the body; and
    a buffer member arranged between the optical device and the skin so that the optical device of the skin side does not come in contact with the skin or pushes the skin with a pressure which is less than a predetermined level.

6. The apparatus according to claim 4, further comprising:
motion artifact determining means which determines an occurrence of a motion artifact based on the pulse waves detected by the sensing means, wherein
the cough determining means determines the occurrence of the cough when the motion artifact determining means additionally determines no occurrence of the motion artifact.

7. An apparatus for detecting vital functions, comprising:
sensing means adapted for attachment to a body and produces pulse wave signals corresponding to pulse waves of the body; and
cough determining means which determines an occurrence of a cough when an amplitude of the pulse waves on a p-systole side corresponding to a systolic phase of a heart of the body has increased by more than a predetermined level without causing a waveform of the pulse waves to be varied from a waveform of ordinary pulse waves which are produced in a calm state of the body.

8. The apparatus according to claim 7, wherein the sensing means includes:
an optical device for projecting light onto a skin of the body to measure the pulse waves of the body; and
a buffer member arranged between the optical device and the skin so that the optical device of the skin side does not come in contact with the skin or pushes the skin with a pressure which is less than a predetermined level.

9. The apparatus according to claim 7, further comprising:
motion artifact determining means which determines an occurrence of a motion artifact based on the pulse waves detected by the sensing means, wherein
the cough determining means determines the occurrence of the cough when the motion artifact determining means additionally determines no occurrence of the motion artifact.

10. An apparatus for detecting vital functions, comprising:
sensing means adapted for attachment to a body and produces pulse wave signals corresponding to pulse waves of the body; and
cough determining means which determines an occurrence of a cough when a change in a ratio AW2/BW2 of an amplitude AW2 of a base level of the pulse waves divided by an amplitude BW2 of the pulse waves is within a predetermined value and within a predetermined period of time corresponding to a coughing.

11. The apparatus according to claim 10, wherein the sensing means includes:
an optical device for projecting light onto a skin of the body to measure the pulse waves of the body; and
a buffer member arranged between the optical device and the skin so that the optical device of the skin side does not come in contact with the skin or pushes the skin with a pressure which is less than a predetermined level.

12. The apparatus according to claim 10, further comprising:
motion artifact determining means which determines an occurrence of a motion artifact based on the pulse waves detected by the sensing means, wherein
the cough determining means determines the occurrence of the cough when the motion artifact determining means additionally determines no occurrence of the motion artifact.

13. An apparatus for detecting vital functions, comprising:
sensing means adapted for attachment to a body and produces pulse wave signals corresponding to pulse waves of the body; and
yawn determining means which determines an occurrence of a yawn when a base level of the pulse waves is lowered over a predetermined period corresponding to yawning.

14. The apparatus according to claim 13, wherein
the yawn determining means determines the occurrence of a yawn when an amplitude of the pulse waves has become smaller than a predetermined level within a period in which the base level of the pulse waves is lower than a predetermined level.

15. An apparatus for detecting vital functions according to claim 14, further comprising:
motion artifact checking means which determines an occurrence of a motion artifact, wherein
the yawn determining means determines the occurrence of the yawn when the motion artifact checking means additionally determines no occurrence of the motion artifact.

16. An apparatus for detecting vital functions according to claim 13, further comprising:
motion artifact checking means which determines an occurrence of a motion artifact, wherein
the yawn determining means determines the occurrence of the yawn when the motion artifact checking means additionally determines no occurrence of the motion artifact.

17. The apparatus according to claim 16, wherein
the motion artifact determining means determines an occurrence of a motion artifact when an amplitude on a p-diastole side corresponding to a diastolic phase of a heart of the body has exceeded a predetermined limit level that corresponds to a diastolic blood pressure of the body.

18. An apparatus according to claim 16 further comprising:
an actuator; and
control means which controls the actuator when the occurrence of the yawn is determined by the yawn determining means.

19. An apparatus for detecting vital functions, comprising:
sensing means adapted for attachment to a body and produces pulse wave signals corresponding to pulse waves of the body; and
yawn determining means which determines an occurrence of a yawn when an amplitude of the pulse waves on a p-systole side corresponding to a systolic phase of a heart of the body exceeds a predetermined level but when an amplitude of a succeeding pulse wave signals on a p-diastole side corresponding to a diastolic phase of the heart of the body does not become smaller than a predetermined level.

20. An apparatus for detecting vital functions according to claim 19 further comprising:
motion artifact checking means which determines an occurrence of a motion artifact, wherein
the yawn determining means determines the occurrence of the yawn when the motion artifact checking means additionally determines no occurrence of the motion artifact.

21. An apparatus for detecting vital functions, comprising:
sensing means adapted for attachment to a body and produces pulse wave signals corresponding to pulse waves of the body; and
yawn determining means which determines an occurrence of a yawn when a whole amplitude of pulse waves of a sum of amplitudes on a p-systole side and of amplitudes on a p-diastole side becomes smaller than a predetermined level after the amplitudes on p-systole side corresponding to the systolic phase of a heart of the body has exceeded a predetermined level without causing the waveform of the pulse waves to be varied from the waveform of ordinary pulse waves.

22. An apparatus for detecting vital functions according to claim 21, further comprising:
   motion artifact checking means which determines an occurrence of a motion artifact, wherein
   the yawn determining means determines the occurrence of the yawn when the motion artifact checking means additionally determines no occurrence of the motion artifact.

23. An apparatus for detecting vital functions, comprising:
   sensing means adapted for attachment to a body and produces pulse wave signals corresponding to pulse waves of the body;
   respiration waveform calculation means which finds a respiration waveform that represents a respiration condition from the pulse waves; and
   yawn determining means which determines an occurrence of a yawn when the amplitude of the respiration waveform is not smaller than a predetermined level and when a double triangular wave of an obtuse angle is detected in which two peaks of the respiration waveform consecutively exceed a predetermined level.

24. An apparatus for detecting vital functions according to claim 23, further comprising:
   motion artifact checking means which determines an occurrence of a motion artifact, wherein
   the yawn determining means determines the occurrence of the yawn when the motion artifact checking means additionally determines no occurrence of the motion artifact.

25. An apparatus for detecting vital functions, comprising:
   sensing means adapted for attachment to a body and produces pulse wave signals corresponding to pulse waves of the body;
   yawn determining means which determines an occurrence of a yawn when a change in a ratio AW2/BW2 of an amplitude AW2 of a base level of the pulse waves divided by an amplitude BW2 of the pulse waves is not smaller than a predetermined level and within a predetermined period of time corresponding to a yawning.

26. An apparatus for detecting vital functions according to claim 25, further comprising:
   motion artifact checking means which determines an occurrence of a motion artifact, wherein
   the yawn determining means determines the occurrence of the yawn when the motion artifact checking means additionally determines no occurrence of the motion artifact.

\* \* \* \* \*